US00PP31033P2

(12) United States Plant Patent
Janes et al.

(10) Patent No.: US PP31,033 P2
(45) Date of Patent: Nov. 5, 2019

(54) ***SALVIA* PLANT NAMED 'BLUE BY YOU'**

(50) Latin Name: ***Salvia* hybrid**
Varietal Denomination: Blue by You

(71) Applicant: Ball Horticultural Company, West Chicago, IL (US)

(72) Inventors: Jessica Diane Janes, Elkton, MD (US); Sloane Michele Scheiber, Parkesburg, PA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/350,043

(22) Filed: Sep. 18, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Anne Marie Grunberg
(74) *Attorney, Agent, or Firm* — Audrey Charles

(57) ABSTRACT

A new and distinct cultivar of *Salvia* plant named 'Blue by You', characterized by its deep violet-blue colored flowers, medium green-colored foliage, and moderately vigorous, upright-mounded growth habit, is disclosed.

2 Drawing Sheets

Latin name of genus and species of plant claimed: *Salvia* hybrid.

Variety denomination: 'Blue by You'.

BACKGROUND OF THE INVENTION

The present invention relates to a new and distinct cultivar of *Salvia* plant botanically known as *Salvia* hybrid and hereinafter referred to by the cultivar name 'Blue by You'.

The new cultivar originated in a controlled breeding program in Cochranville, Pa. during June 2011. The objective of the breeding program was the development of sterile *Salvia* cultivars with good repeat blooming, and excellent weather tolerance.

The new *Salvia* cultivar was the result of cross-pollination. The female (seed) parent of the new cultivar is *Salvia nemorosa* 'May Night', also known as 'Mainacht', not patented, characterized by its dark violet-colored flowers, medium green-colored foliage, and moderately vigorous, semi-upright growth habit. The male (pollen) parent of the new cultivar is *Salvia pratensis* 'Rose Rhapsody', not patented, characterized by its medium pink-colored flowers, medium green-colored foliage, and moderately vigorous, semi-upright growth habit. The new cultivar was discovered and selected as a single flowering plant within the progeny of the above stated cross-pollination during July 2012 in a controlled environment in Cochranville, Pa.

Asexual reproduction of the new cultivar by terminal stem cuttings since July 2012 in Cochranville, Pa. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Blue by You' as a new and distinct cultivar of *Salvia* plant:

1. Deep violet-blue colored flowers;
2. Medium green-colored foliage; and
3. Moderately vigorous, upright-mounded growth habit.

Plants of the new cultivar differ from plants of the female parent primarily in having larger flowers and larger foliage. Plants of the new cultivar differ from plants of the male parent primarily in having a different flower color and more mounded growth habit.

Of the many commercially available *Salvia* cultivars, the most similar in comparison to the new cultivar is FASHIONISTA 'Midnight Model', U.S. Plant Pat. No. 29,498. However, in side by side comparisons, plants of the new cultivar differ from plants of 'Midnight Model' in at least the following characteristics:

1. Plants of the new cultivar have smaller corollas than plants of 'Midnight Model';
2. Plants of the new cultivar have a darker flower color than plants of 'Midnight Model'; and
3. Plants of the new cultivar is male-sterile unlike plants of 'Midnight Model'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Blue by You'. The plants were approximately four months old. The plants were grown in one-gallon containers for approximately 9 weeks in a greenhouse in Elburn, Ill. followed by 1 week in an open-sided polyhouse in West Chicago, Ill. Plants were given two pinches, one at one week before transplant and one two weeks after transplant.

DETAILED BOTANICAL DESCRIPTION

Figure 1:
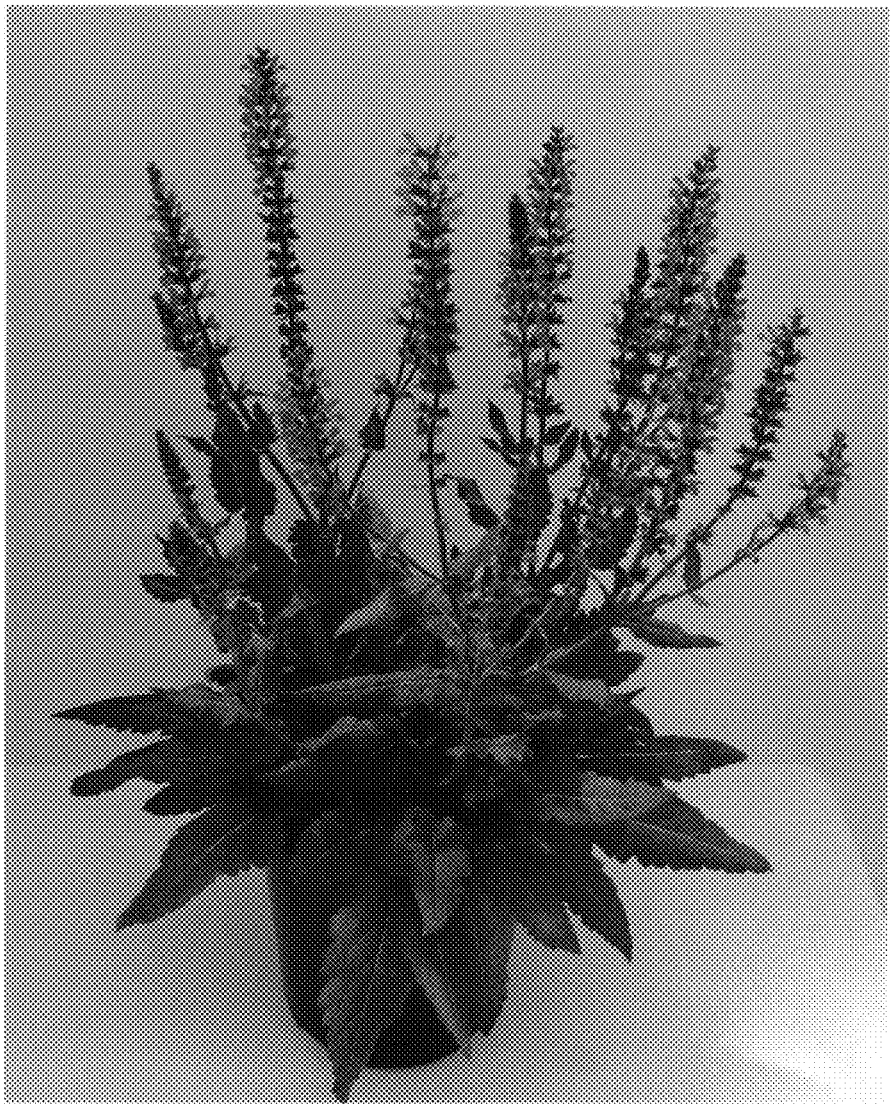
FIG. 1 illustrates a side view of the overall growth and flowering habit of 'Blue by You'.
Figure 2:
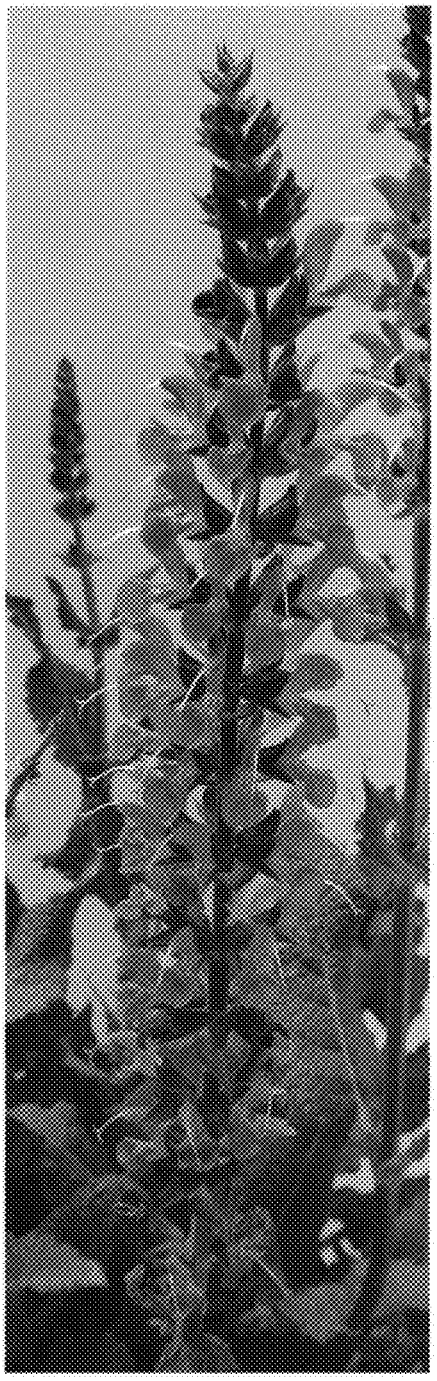
FIG. 2 illustrates a close-up view of an individual inflorescence of 'Blue by You'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 9 weeks in a greenhouse in Elburn, Ill. followed by 2 weeks in an open-sided polyhouse in West Chicago, Ill. Plants were given two pinches, one at one week before transplant and one two weeks after transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Salvia* hybrid 'Blue by You'.

Parentage:

*Female parent.*—*Salvia nemorosa* 'May Night', also known as 'Mainacht', not patented.

*Male parent.*—*Salvia pratensis* 'Rose Rhapsody', not patented.

Propagation:

*Type cutting.*—Terminal stem.

*Time to initiate roots.*—Approximately 12 to 15 days.

*Time to produce a rooted cutting.*—Approximately 35 to 42 days.

*Root description.*—Fine, fibrous.

*Rooting habit.*—Freely branching.

Plant description:

*Commercial crop time.*—Approximately 10 to 12 weeks from a rooted cutting to finish in a 15 cm pot.

*Growth habit and general appearance.*—Herbaceous perennial, moderately vigorous, upright-mounded growth habit.

*Hardiness.*—USDA Zone 4b (−25° F. to −20° F./−31.7° C. to −28.9° C.).

*Size.*—Height from soil level to top of plant plane: Approximately 38.0 cm. Width: Approximately 40.0 cm.

*Branching habit.*—Freely branching. Pinching enhances lateral branching. Quantity of branches per plant: Approximately 5.

*Branch.*—Shape: Square in cross section. Strength: Strong. Length to base of inflorescence: Approximately 13.5 cm. Diameter: Approximately 4.0 mm. Length of central internode: Approximately 6.0 cm. Texture: Densely pubescent with short appressed hairs. Color of young stems: 146D. Color of mature stems: 146B tinted with 187A in sun.

Foliage description:

*General description.*—Quantity of leaves per main branch: Approximately 6. Fragrance: Strong, sage-like. Form: Simple. Arrangement: Opposite.

*Leaves.*—Aspect: Acute to perpendicular angle to stem. Shape: Lanceolate. Margin: Crenate. Apex: Acute. Base: Cordate. Venation pattern: Pinnate. Length of mature leaf: Approximately 13.0 cm. Width of mature leaf: Approximately 4.5 cm. Texture of upper surface: Rugose, moderately pubescent only on midvein. Texture of lower surface: Rugose, moderately pubescent only on venation. Color of upper surface of young and mature foliage: Closest to 137A with venation of 145D. Color of lower surface of mature foliage: Closest to 137C with venation of 147D.

*Petiole.*—Length: Approximately 11.0 cm. Diameter: Approximately 4.0 mm. Texture: Densely pubescent with appressed hairs. Color: Closest to 147D.

Flowering description:

*Flowering habit.*—'Blue by You' is freely flowering under outdoor growing conditions with substantially continuous blooming from spring through late summer and with limited flowering under short winter days in a greenhouse environment.

*Lastingness of individual floret.*—Approximately 4 to 5 days.

Inflorescence description:

*General description.*—Type: Spikes in verticillaster arrangement, florets in clusters of two to three, not persistent. Quantity of inflorescences per plant: Approximately 15. Fragrance: Faint, sweet. Length or height of inflorescence: Approximately 7.0 cm to 17.0 cm. Width of inflorescence: Approximately 2.5 cm to 3.0 cm. Quantity of fully-open flowers per inflorescence: Approximately 20 with up to 48 at peak flowering.

*Peduncle.*—Shape: Square in cross section. Strength: Strong. Aspect: Erect. Length: Approximately 2.7 cm to 4.0 cm. Diameter: Approximately 2.0 mm to 4.0 mm. Texture: Densely pubescent. Color: 146B tinted with 187A in sun.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 7.0 mm. Diameter: Approximately 4.0 mm. Texture: Densely pubescent. Color: Calyx of 146C to 146D with an overlay of 187A on tips; petal portion of N89A.

*Corolla.*—Shape: Bilabiate, lower lip having three lobes, base fused. Width: Approximately 6.0 mm. Length: Approximately 1.1 cm. Depth: Approximately 1.7 cm.

*Upper lip.*—Shape: Hooded. Margin: Entire. Apex: Rounded. Length from throat: Approximately 1.1 cm. Width: Approximately 1.0 mm. Texture of inner surface: Glabrous. Texture of outer surface: Moderately pubescent. Color of inner surface when first and fully open: 91A. Color of outer surface when first and fully open: N88A to N88C, darker shade predominates under full sun conditions.

*Lower lip.*—Shape of central lobe: Orbicular, cupped. Shape of lateral lobes: Oblong. Margin: Entire, central lobe wavy. Apex of central lobe: Emarginate.

Apex of lateral lobes: Rounded. Length from throat of central lobe: Approximately 5.0 mm. Width of central lobe: Approximately 7.0 mm. Length from throat of lateral lobes: Approximately 3.0 mm. Width of lateral lobes: Approximately 1.0 mm. Texture of upper surface: Glabrous. Texture of lower surface: Sparsely pubescent. Color of upper surface of lateral and central lobes when first and fully open: N89B to N89C, darker shade predominates under full sun conditions. Color of lower surface of lateral and central lobes when first and fully open: Closest to N89C to N89D.

*Corolla tube*.—Length: Approximately 6.0 mm. Diameter at opening: Approximately 4.0 mm. Diameter at base: Approximately 2.0 mm. Texture of inner and outer surfaces: Glabrous. Color of inner surface when first and fully open: NN155D. Color of outer surface when first and fully open: NN155D tinted with N89D.

*Calyx*.—Shape: Cupped. Length: Approximately 7.0 mm. Diameter: Approximately 5.0 mm.

*Sepals*.—Quantity per flower: 5, fused. Shape: Ovate. Apex: Acute. Length: Approximately 7.0 mm. Width of lobes: Approximately 2.0 mm to 4.0 mm. Texture of inner surfaces: Glabrous. Texture of outer surfaces: Densely pubescent. Color of inner surface: 146D. Color of outer surface: 146C to 146D with an overlay of 187A on tips and venation.

*Bracts*.—Quantity: One bract located at the base of floret cluster. Shape: Ovate. Apex: Acuminate. Texture of upper and lower surfaces: Densely pubescent. Color of inner and outer surfaces: 145B with an overlay of 187A.

*Pedicel*.—Strength: Strong, flexible. Aspect: At an acute angle. Length: Approximately 3.0 mm. Diameter: Less than 1.0 mm. Texture: Densely pubescent. Color: 146D tinted with 187A.

*Reproductive organs*.—Androecium: Stamen quantity: 2 per flower, dorsifixed, strongly curved. Stamen length: Approximately 4.0 mm. Filament length: Approximately 3.0 mm. Filament color: NN155D with a faint overlay of N89D. Anther shape: Oblong. Anther length: Approximately 1.0 mm. Anther color: 161B. Pollen amount: Not observed. Gynoecium: Pistil quantity: 1 per flower, slightly curved. Pistil length: Approximately 1.7 cm. Stigma shape: Cleft, two-parted. Stigma length: 2.0 mm. Stigma color: N88B. Style length: Approximately 1.3 cm. Style color: NN155D. Ovary length: Approximately 2.0 mm. Ovary color: 144B with 158D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Blue by You', substantially as herein illustrated and described.

* * * * *